(12) United States Patent
Christensen et al.

(10) Patent No.: US 7,824,446 B2
(45) Date of Patent: Nov. 2, 2010

(54) PROSTHETIC FOOT WITH LONGER UPPER FOREFOOT AND SHORTER LOWER FOREFOOT

(75) Inventors: Roland J. Christensen, Faytette, UT (US); Marcus Boren, Sterling, UT (US)

(73) Assignee: Freedom Innovations, LLC, Irvine, CA (US)

( * ) Notice: Subject to any disclaimer, the term of this patent is extended or adjusted under 35 U.S.C. 154(b) by 125 days.

(21) Appl. No.: 11/999,734

(22) Filed: Dec. 5, 2007

(65) Prior Publication Data

US 2008/0167731 A1 Jul. 10, 2008

Related U.S. Application Data

(60) Provisional application No. 60/873,402, filed on Dec. 6, 2006.

(51) Int. Cl.
*A61F 2/66* (2006.01)
*A61F 2/68* (2006.01)

(52) U.S. Cl. .......................................... 623/52; 623/55
(58) Field of Classification Search ............. 623/47–56; 482/75–76
See application file for complete search history.

(56) References Cited

U.S. PATENT DOCUMENTS

| | | |
|---|---|---|
| 42,799 A | 5/1864 | Shepard |
| 92,031 A | 6/1869 | Foster |
| 292,800 A | 2/1884 | Furrer |
| 497,026 A | 5/1893 | Judson |
| 1,001,641 A | 8/1911 | Harrison |
| 1,289,580 A | 12/1918 | Vincenti |
| 1,779,765 A | 10/1930 | Eichhorn |
| 1,996,874 A | 4/1935 | Mascau |
| 2,036,830 A | 4/1936 | Rowley |
| 2,379,538 A | 7/1945 | Meierhofer |
| 2,443,356 A | 6/1948 | Mathis |
| 2,453,969 A | 11/1948 | Carter |

(Continued)

FOREIGN PATENT DOCUMENTS

BR          9304552          7/1995

(Continued)

OTHER PUBLICATIONS www.micacorp.com/products/genesis2/, MICA Manufacturing Corporation, Genesis II Prosthetic Foot, Nov. 24, 2004, 1 page.

(Continued)

*Primary Examiner*—William H Matthews
*Assistant Examiner*—Marcia Hoffman
(74) *Attorney, Agent, or Firm*—Thorpe North & Western LLP

(57) ABSTRACT

The invention provides a prosthetic foot device including an elongated upper forefoot portion extending through an upper attachment section, forwardly through an arch section, and to a toe section positioned at a toe location of a natural foot. The foot device also includes an elongated lower forefoot portion extending through an upper attachment section attached to the attachment section of the upper forefoot portion, and forwardly under the arch section of the upper forefoot portion to a terminal end positioned under the ball location of a natural foot and rearward of the toe section of the upper forefoot portion.

19 Claims, 9 Drawing Sheets

U.S. PATENT DOCUMENTS

| | | | |
|---|---|---|---|
| 2,470,480 | A | 5/1949 | Fogg |
| 2,570,735 | A | 10/1951 | Weise |
| 2,617,115 | A | 11/1952 | Ellery |
| 2,640,200 | A | 6/1953 | Wisbrun |
| 2,843,853 | A | 7/1958 | Mauch |
| 3,206,235 | A | 9/1965 | Albinson et al. |
| 3,548,420 | A | 12/1970 | Spence |
| 3,551,914 | A | 1/1971 | Woodall |
| 3,754,286 | A | 8/1973 | Ryan |
| 3,858,379 | A | 1/1975 | Graves et al. |
| 3,871,032 | A | 3/1975 | Karas |
| 3,874,004 | A | 4/1975 | May |
| 3,906,552 | A | 9/1975 | Weber |
| 3,920,610 | A | 11/1975 | Wagner |
| 3,956,775 | A | 5/1976 | Moore |
| 3,982,280 | A | 9/1976 | Asbelle et al. |
| 4,089,072 | A | 5/1978 | Glabiszewski |
| 4,328,594 | A | 5/1982 | Campbell et al. |
| 4,442,554 | A | 4/1984 | Copes |
| 4,506,395 | A | 3/1985 | Haupt |
| 4,547,913 | A | 10/1985 | Phillips |
| 4,606,332 | A | 8/1986 | Gibson |
| 4,636,220 | A | 1/1987 | Ziegelmeyer |
| 4,645,509 | A | 2/1987 | Poggi et al. |
| 4,676,800 | A | 6/1987 | Chen |
| 4,676,801 | A | 6/1987 | Lundeen |
| 4,721,510 | A | 1/1988 | Cooper et al. |
| 4,764,172 | A | 8/1988 | McCoy |
| 4,822,363 | A | 4/1989 | Phillips |
| 4,865,611 | A | 9/1989 | Al-Turaiki |
| 4,865,612 | A | 9/1989 | Arbogast et al. |
| 4,892,553 | A * | 1/1990 | Prahl .................. 623/55 |
| 4,938,775 | A | 7/1990 | Morgan |
| 4,959,073 | A | 9/1990 | Merlette |
| 5,007,938 | A * | 4/1991 | Prahl .................. 623/55 |
| 5,019,109 | A | 5/1991 | Voisin |
| 5,030,239 | A | 7/1991 | Copes |
| 5,037,444 | A | 8/1991 | Phillips |
| 5,062,859 | A | 11/1991 | Naeder |
| 5,112,356 | A | 5/1992 | Harris et al. |
| 5,116,383 | A | 5/1992 | Shorter et al. |
| 5,116,384 | A | 5/1992 | Wilson et al. |
| 5,156,632 | A | 10/1992 | Wellershaus |
| 5,181,932 | A | 1/1993 | Phillips |
| 5,181,933 | A | 1/1993 | Phillips |
| 5,217,500 | A | 6/1993 | Phillips |
| 5,219,365 | A | 6/1993 | Sabolich |
| 5,258,039 | A | 11/1993 | Goh et al. |
| 5,267,633 | A | 12/1993 | Endo et al. |
| 5,290,319 | A | 3/1994 | Phillips |
| 5,314,499 | A | 5/1994 | Collier, Jr. |
| 5,376,133 | A | 12/1994 | Gramnas |
| 5,376,139 | A | 12/1994 | Pitkin |
| 5,376,141 | A | 12/1994 | Phillips |
| 5,387,246 | A | 2/1995 | Phillips |
| 5,405,411 | A | 4/1995 | McCoy |
| 5,425,781 | A | 6/1995 | Allard et al. |
| 5,425,782 | A | 6/1995 | Phillips |
| 5,443,528 | A | 8/1995 | Allen |
| 5,443,529 | A | 8/1995 | Phillips |
| 5,458,656 | A | 10/1995 | Phillips |
| 5,464,441 | A | 11/1995 | Phillips |
| 5,482,513 | A | 1/1996 | Wilson |
| 5,486,209 | A | 1/1996 | Phillips |
| 5,507,838 | A | 4/1996 | Chen |
| 5,509,936 | A | 4/1996 | Rappoport et al. |
| 5,509,937 | A | 4/1996 | Allard et al. |
| 5,509,938 | A | 4/1996 | Phillips |
| 5,514,185 | A | 5/1996 | Phillips |
| 5,514,186 | A | 5/1996 | Phillips |
| 5,549,714 | A | 8/1996 | Phillips |
| 5,571,210 | A | 11/1996 | Lindh |
| 5,571,213 | A | 11/1996 | Allen |
| 5,593,455 | A | 1/1997 | Phillips |
| 5,593,456 | A | 1/1997 | Merlette |
| 5,593,457 | A | 1/1997 | Phillips |
| 5,653,767 | A | 8/1997 | Allen et al. |
| 5,653,768 | A | 8/1997 | Kania |
| 5,725,598 | A | 3/1998 | Phillips |
| 5,728,175 | A | 3/1998 | Rincoe |
| 5,728,176 | A | 3/1998 | Phillips |
| 5,728,177 | A | 3/1998 | Phillips |
| 5,746,774 | A | 5/1998 | Kramer et al. |
| 5,766,265 | A | 6/1998 | Phillips |
| 5,766,704 | A | 6/1998 | Allen et al. |
| 5,769,896 | A | 6/1998 | Rosendahl et al. |
| 5,776,205 | A | 7/1998 | Phillips |
| 5,779,735 | A | 7/1998 | Molino |
| 5,800,564 | A | 9/1998 | Gelineau |
| 5,800,565 | A | 9/1998 | Biedermann |
| 5,800,569 | A | 9/1998 | Phillips |
| 5,824,112 | A | 10/1998 | Phillips |
| 5,888,238 | A | 3/1999 | Phillips et al. |
| 5,888,239 | A * | 3/1999 | Wellershaus et al. .......... 623/55 |
| 5,893,891 | A | 4/1999 | Zahedi |
| 5,899,944 | A | 5/1999 | Phillips |
| 5,913,902 | A | 6/1999 | Geible |
| 5,944,760 | A | 8/1999 | Christensen |
| 5,957,981 | A | 9/1999 | Gramnas |
| 5,976,191 | A | 11/1999 | Phillips |
| 5,993,488 | A | 11/1999 | Phillips |
| 6,007,582 | A | 12/1999 | May |
| 6,019,795 | A | 2/2000 | Phillips |
| 6,071,313 | A | 6/2000 | Phillips |
| 6,077,301 | A | 6/2000 | Pusch |
| 6,099,572 | A | 8/2000 | Mosler et al. |
| 6,120,547 | A | 9/2000 | Christensen |
| 6,165,227 | A | 12/2000 | Phillips |
| 6,187,052 | B1 | 2/2001 | Molino et al. |
| 6,197,068 | B1 | 3/2001 | Christensen |
| 6,206,934 | B1 | 3/2001 | Phillips |
| 6,228,124 | B1 | 5/2001 | Slemker et al. |
| 6,241,776 | B1 | 6/2001 | Christensen |
| 6,254,643 | B1 | 7/2001 | Phillips |
| 6,261,324 | B1 | 7/2001 | Merlette |
| 6,280,479 | B1 | 8/2001 | Phillips |
| 6,290,730 | B1 | 9/2001 | Pitkin et al. |
| 6,306,178 | B1 | 10/2001 | Kania et al. |
| 6,402,790 | B1 | 6/2002 | Celebi |
| 6,406,500 | B1 | 6/2002 | Phillips |
| 6,443,993 | B1 | 9/2002 | Koniuk |
| 6,443,995 | B1 | 9/2002 | Townsend et al. |
| 6,514,293 | B1 | 2/2003 | Jang et al. |
| 6,562,075 | B2 | 5/2003 | Townsend et al. |
| 6,596,029 | B1 | 7/2003 | Gramnas |
| 6,602,295 | B1 | 8/2003 | Doddroe et al. |
| 6,663,673 | B2 | 12/2003 | Christensen |
| 6,669,737 | B2 | 12/2003 | Mosler et al. |
| 6,676,708 | B2 | 1/2004 | Laghi |
| 6,740,125 | B2 | 5/2004 | Mosler |
| 6,793,683 | B1 | 9/2004 | Laghi |
| 6,805,717 | B2 | 10/2004 | Christensen |
| 6,869,451 | B1 | 3/2005 | Laghi |
| 6,875,241 | B2 | 4/2005 | Christensen |
| 6,875,242 | B2 | 4/2005 | Christensen |
| 6,887,279 | B2 | 5/2005 | Phillips et al. |
| 6,911,052 | B2 | 6/2005 | Christensen |
| 6,929,665 | B2 | 8/2005 | Christensen |
| 6,966,933 | B2 | 11/2005 | Christensen |
| 7,172,630 | B2 | 2/2007 | Christensen |
| 7,341,603 | B2 | 3/2008 | Christensen |
| 7,347,877 | B2 * | 3/2008 | Clausen et al. ................ 623/52 |
| 2002/0077706 | A1 | 6/2002 | Phillips |
| 2002/0133237 | A1 | 9/2002 | Christesen |

| | | | | | | |
|---|---|---|---|---|---|---|
| 2003/0019540 | A1 | 1/2003 | Townsend et al. | GB | 1550658 | 11/1976 |
| 2003/0045944 | A1 | 3/2003 | Mosler et al. | GB | 2244006 | 11/1991 |
| 2004/0068326 | A1 | 4/2004 | Christensen | IT | 556381 | 2/1957 |
| 2004/0162623 | A1 | 8/2004 | Phillips | RU | 2033772 | 4/1995 |
| 2005/0049721 | A1 | 3/2005 | Sulprizio | SU | 560606 | 6/1977 |
| 2005/0187640 | A1 | 8/2005 | Christensen | WO | WO 94 10942 | 5/1994 |
| 2005/0203640 | A1 | 9/2005 | Christensen | WO | WO 02 30340 | 4/2002 |
| 2006/0030950 | A1 | 2/2006 | Townsend | WO | WO03/003953 | 1/2003 |
| 2009/0265019 | A1 | 10/2009 | Christensen | | | |

FOREIGN PATENT DOCUMENTS

| | | |
|---|---|---|
| BR | 9304225 | 11/1995 |
| DE | 295807 | * 12/1916 |
| EP | 1 149 568 | 10/2001 |
| EP | 1340478 | 9/2003 |
| GB | 1191633 | 5/1970 |

OTHER PUBLICATIONS www.oandp.org/jpo/library/2000_01_009.asp, "Comparison od the seattle lite foot and genesis II prosthetic foot during walking and running." Americann Academy of Orthotists and Prosthetists, 2000, pp. 9-14, vol. 12, No. 1.

* cited by examiner

PROSTHETIC FOOT WITH LONGER UPPER FOREFOOT AND SHORTER LOWER FOREFOOT

PRIORITY CLAIM

Benefit is clamed of U.S. Provisional Patent Application Ser. No. 60/873,402, filed Dec. 6, 2006, which is herein incorporated by reference in its entirety for all purposes.

BACKGROUND OF THE INVENTION

1. Field of the Invention

The present invention relates generally to foot prosthetic devices.

2. Related Art

Many individuals have lost a limb for various reasons including war, accident, or disease. In most instances these individuals are not only able to live relatively normal lives, but physically active lives as well. Often times, these individuals are aided in their everyday lives by a prosthetic limb. The objective of prosthesis is to provide an artificial limb that simulates the function and natural feel of the replaced limb.

With respect to prosthetic feet, the development of a functional and natural artificial foot has been limited only by material and imagination. Many designs have attempted to copy the anatomy of the foot or simulate its actions by replacing the bones and muscle with various mechanical components. Other designs have departed radically from mere anatomical copying or mechanical simulation by replacing the entire foot with an energy storage element, such as a spring. As the user steps onto the foot, the user's weight compresses the spring. As the user moves forward, the user's weight comes off the foot and the energy stored in the spring is used to propel the user forward.

In addition, the performance of these energy storing feet has been altered in various ways, such as by using multiple springs with a primary spring and a secondary spring that deflect at different intervals of foot deflection to add resistance. Unfortunately, such multiple spring feet have not provided the stiff resiliency desired through high load portions of a user's gait while still allowing the foot to have a softer resiliency when the user assumes a terminal stance.

SUMMARY OF THE INVENTION

It has been recognized that it would be advantageous to develop a method and device for providing multiple energy storage elements in a prosthetic foot that are independently or corroboratively engageable to provide differing resistive energy to a user during stepping motions and standing positions. It has also been recognized that it would be advantageous to develop a prosthetic foot device that can provide more resistance during high load portions of a user's gait and less resistance when in a terminal stance.

The invention provides a prosthetic foot device including an elongated upper forefoot portion extending 1) through an upper attachment section configured to be coupled to a limb of an amputee, 2) forwardly through an arch section, and 3) to a toe section positioned at a toe location of a natural foot. The foot device also includes an elongated lower forefoot portion extending 1) through an upper attachment section attached to the attachment section of the forefoot portion, and 2) forwardly under the ankle section of the forefoot portion to a terminal end positioned at a ball location of a natural foot and rearward of the toe section of the upper forefoot portion.

Additional features and advantages of the invention will be apparent from the detailed description which follows, taken in conjunction with the accompanying drawings, which together illustrate, by way of example, features of the invention.

DETAILED DESCRIPTION

Figure 1:
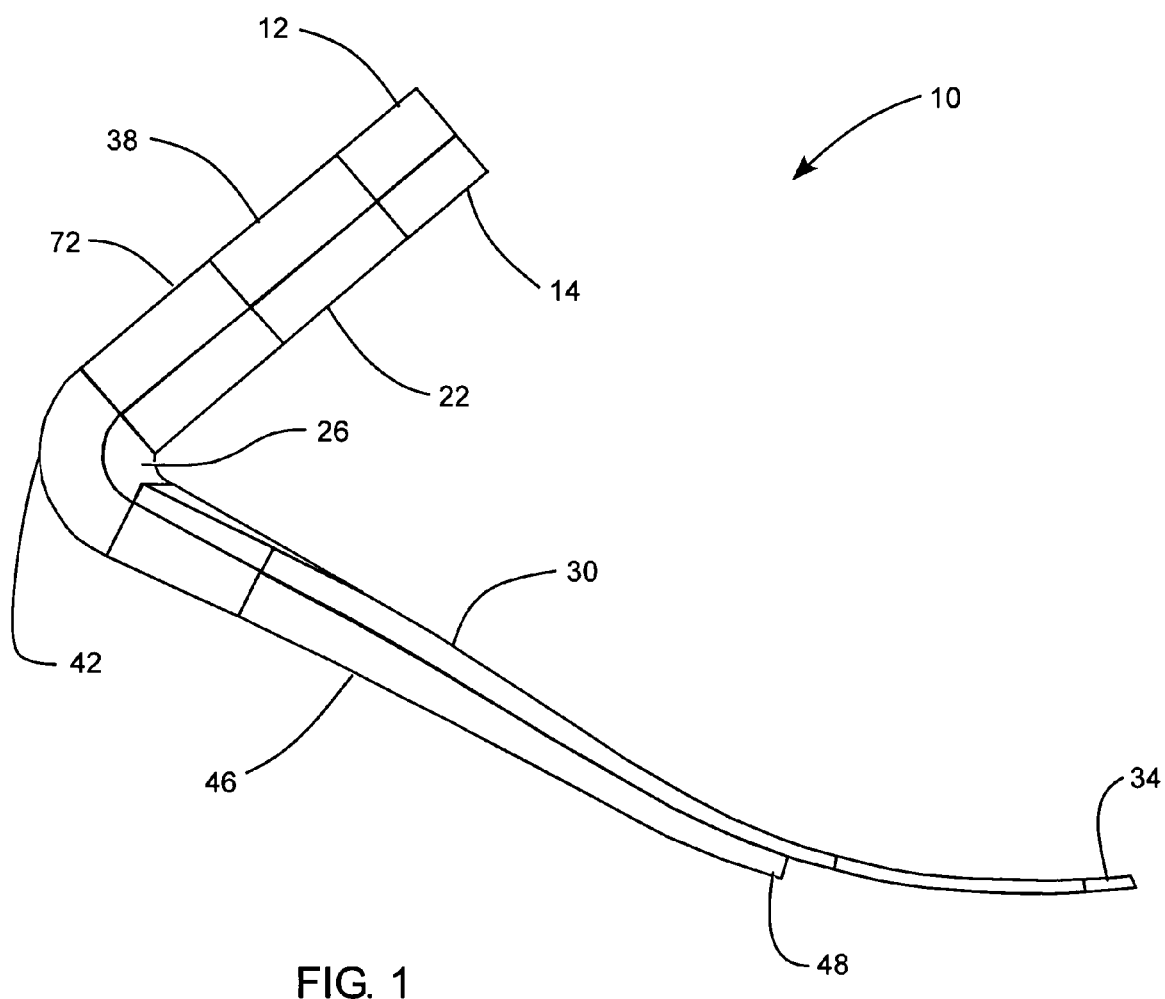
FIG. 1 is a side view of a prosthetic foot device in accordance with an embodiment of the present invention.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

The present invention provides generally for a prosthetic foot having a longer upper elongated forefoot and a shorter lower elongated forefoot. The upper forefoot extends through an attachment section, downward through an ankle section, and forward through an arch section to a toe section positioned at a toe location of a natural foot. The lower forefoot member extends through an attachment section, downward through an ankle section, and forwardly under the arch section of the forefoot portion to a terminal end positioned under the arch section and at a ball location of a natural foot. The terminal end of the lower forefoot member is also positioned rearward of the toe section. Thus, the lower elongated forefoot member is shorter than the upper elongated forefoot member so that the upper forefoot member contacts the ground at the toe section and the lower forefoot member contacts the ground at the ball section.

As illustrated in FIG. 1, a prosthetic foot device, indicated generally at 10, in accordance with the present invention is shown for absorbing shock and cushioning a limb or stump of an amputee. The prosthetic foot 10 can include an elongated, lower forefoot portion 12 and an elongated, upper forefoot portion 14. The lower forefoot portion 12 and upper forefoot portion 14 advantageously form resilient spring members to absorb shock during a walking gait or motion, and cushion the stump or limb of the amputee. The upper forefoot portion 14 can be longer, or can extend past a termination of the lower forefoot portion 12.

The upper forefoot portion 14 can include an upper attachment section 22 to be coupled to the limb or stump of the amputee. The upper forefoot portion 14 can extend downwardly through the attachment section 22, through an ankle section 26, forwardly and downwardly through an arch section 30, and forwardly to a toe section 34. The upper attachment section 22 and the arch section 30 can be substantially straight. The ankle section 26 is positioned at an approximate ankle location of a natural foot. Likewise, the toe section 34 is positioned at an approximate toe location of a natural foot. The ankle location is a region near the rearward end of the foot where an ankle of a natural foot would be located. Similarly, arch, ball, and toe locations are a regions near the middle and forward end of the foot where an arch, ball, toes of a natural foot would be located.

The ankle section 26 of the upper forefoot portion 14 can be substantially arcuate. The arc formed by the ankle section can be smoothly curved, or can be formed of both straight and curved sections. The upper forefoot portion 14 or ankle 26 forms a vertically oriented arc extending between the attachment section 22 and the arch or toe sections. Thus, the upper forefoot portion 14 or ankle section 26 can form a curvilinear spring portion.

The lower forefoot portion 12 includes an upper attachment section 38 attached to the attachment section 22 of the upper forefoot portion 14. The lower forefoot portion 12 extends downwardly through the attachment section 38, through an ankle section 42, forwardly and downwardly past the arch section 46 to a terminal end 48 positioned at the approximate ball location of a natural foot. Similar to the upper forefoot portion 14, the attachment section 38 and the arch section 46 can be substantially straight, and the ankle section 42 can be curved.

Figure 2:
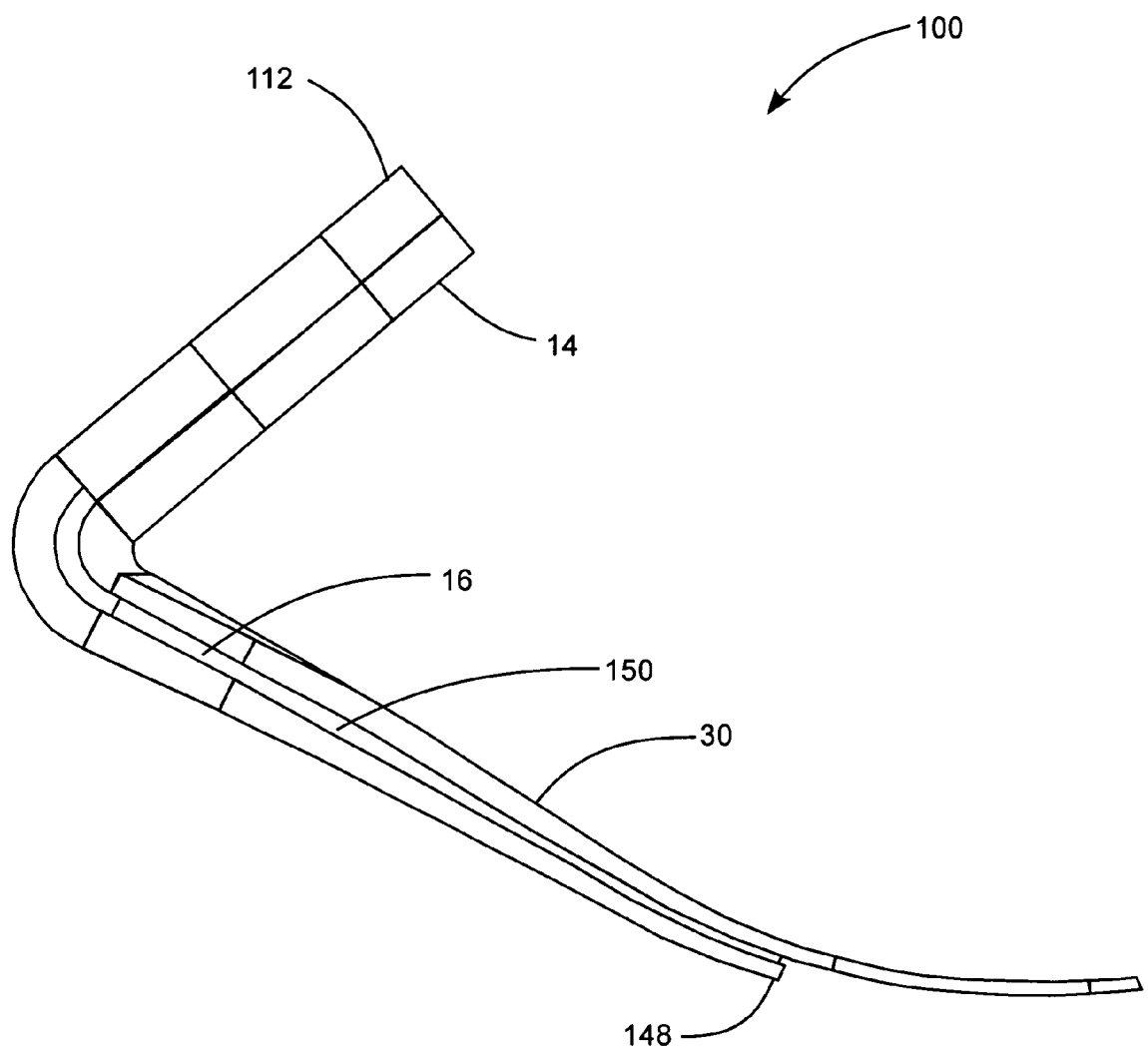
FIG. 2 is a side view of a prosthetic foot device in accordance with another embodiment of the present invention.
Figure 3:
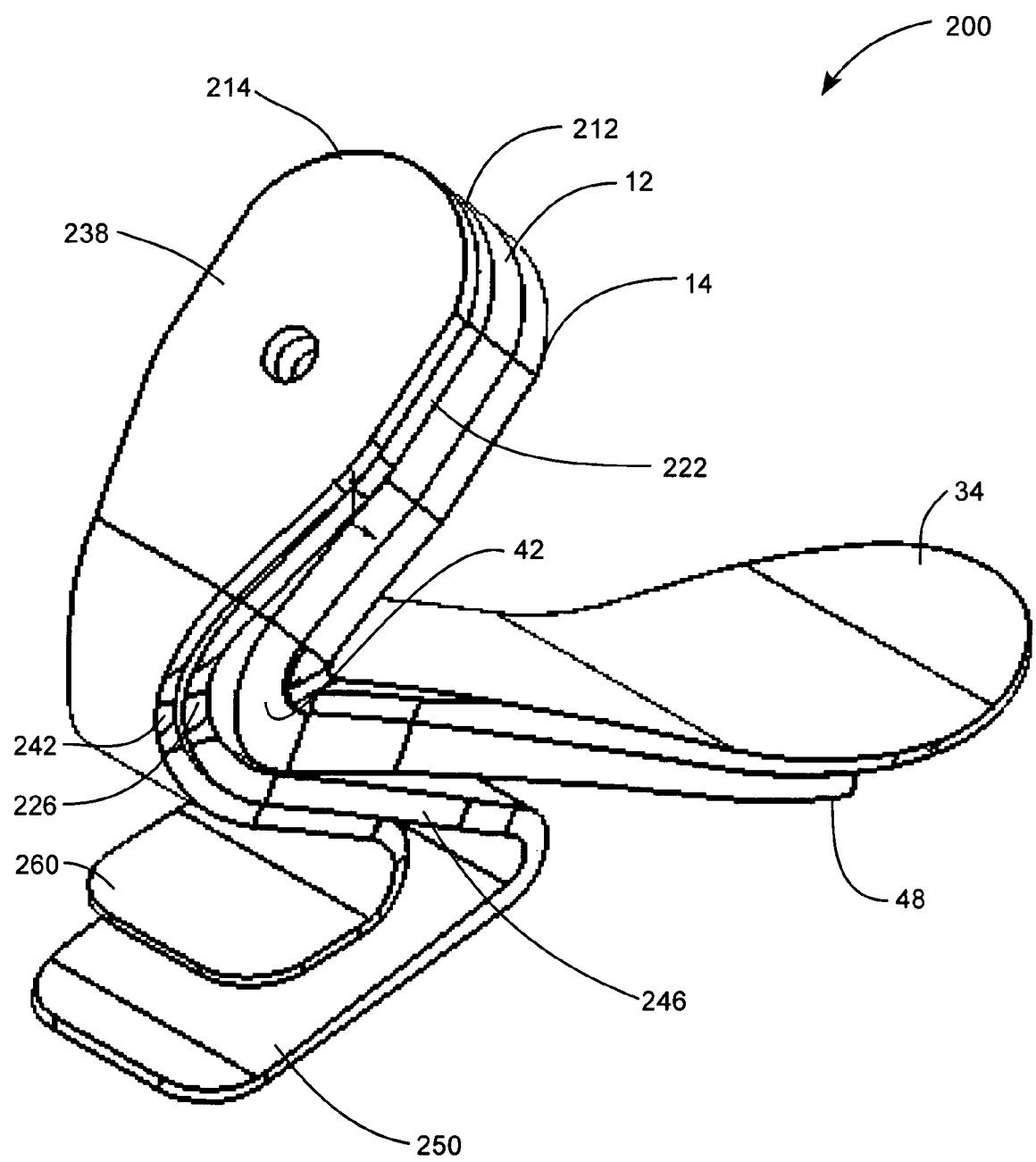
FIG. 3 is a rear perspective view of a prosthetic foot device in accordance with another embodiment of the present invention.
Figure 4:
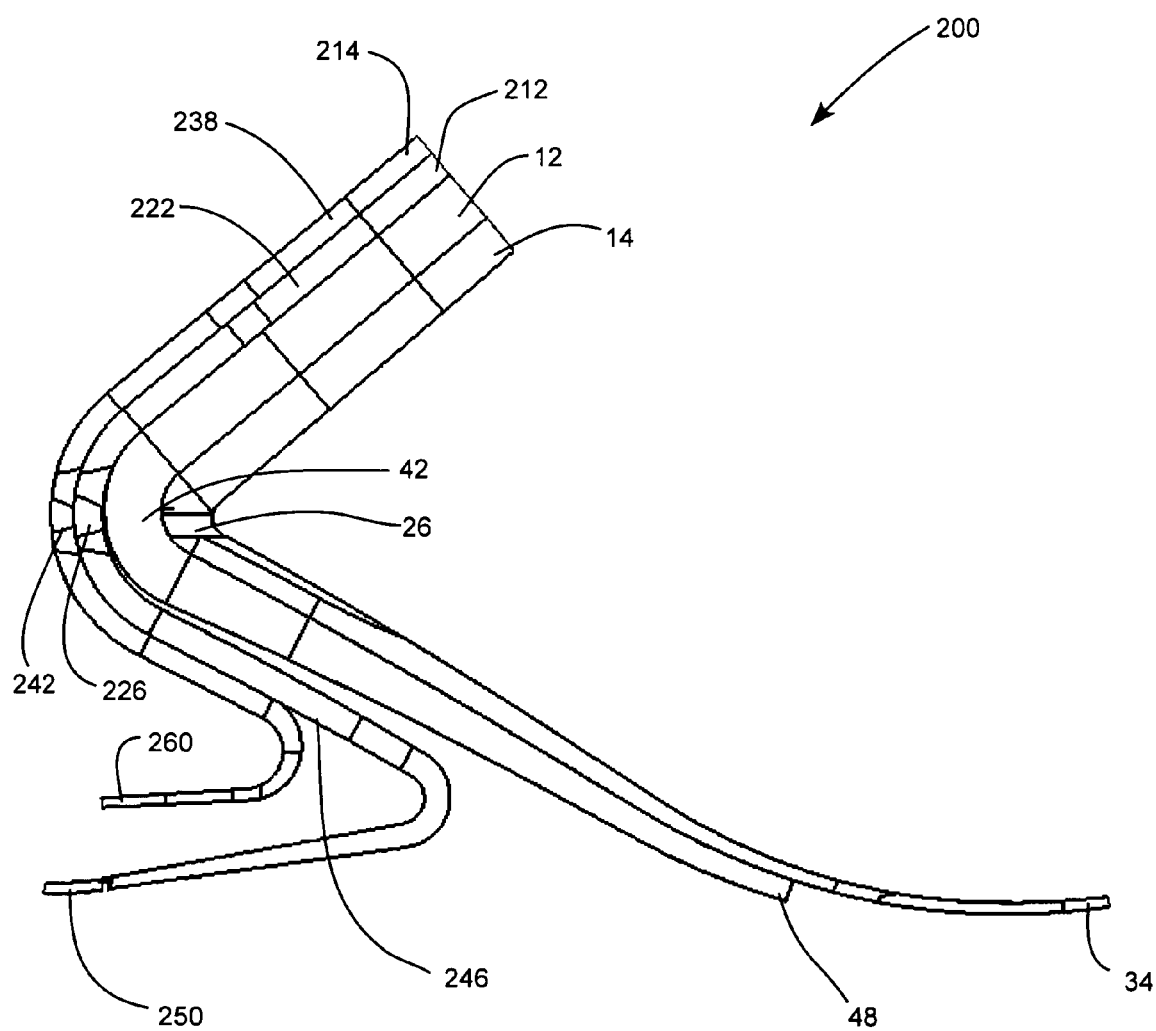
FIG. 4 is a side view of the prosthetic foot device of FIG. 3.
Figure 5:
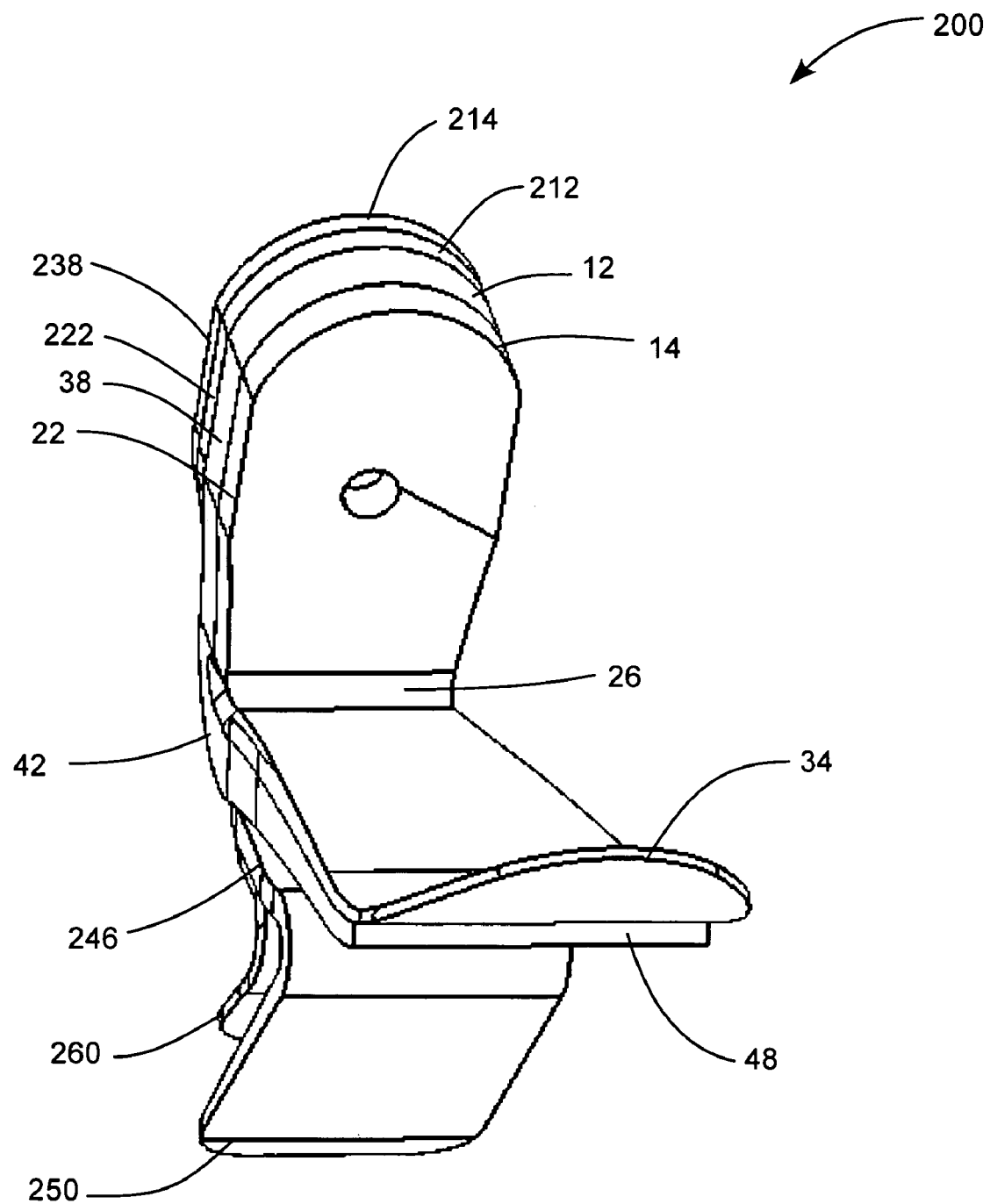
FIG. 5 is a front perspective view of the prosthetic foot device of FIG. 3.
Figure 6:
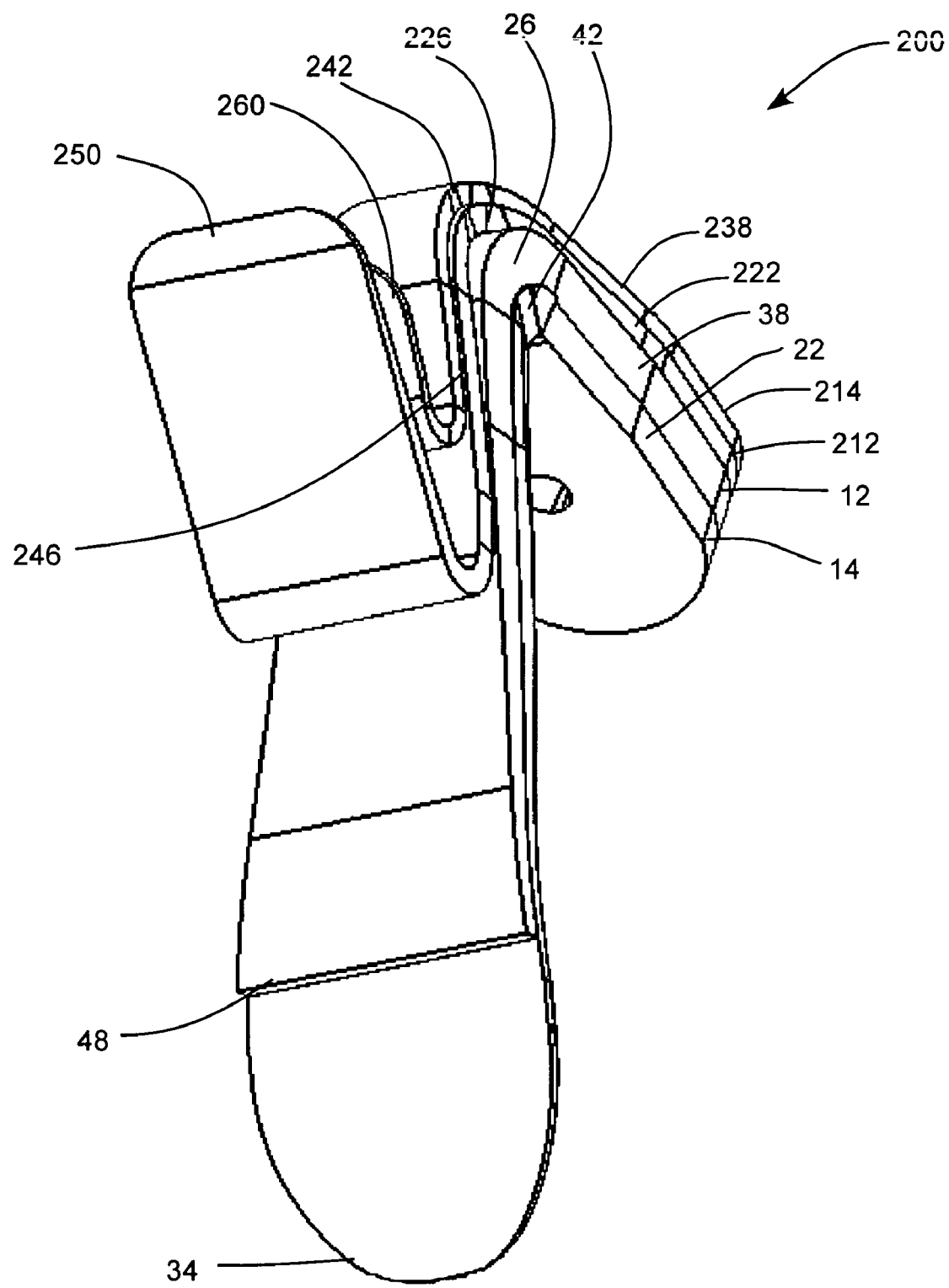
FIG. 6 is a bottom perspective view of the prosthetic foot device of FIG. 3.

The lower forefoot portion 12 can be disposed under the upper forefoot portion 14 from at least the ankle section 42 to the terminal end 48. In one aspect, the upper forefoot portion 14 and lower forefoot portion can be positioned directly adjacent one another with no space or gap between the upper and lower forefoot portions, as shown in FIG. 1. In another aspect, as shown in FIG. 2, the upper forefoot portion 14 and lower forefoot portion 12 can be spaced apart from one another such that a gap 16 can be formed between the upper and lower forefoot portions. As discussed below, the gap 16 can be filled with an energy storing material.

Returning to FIG. 1, the terminal end 48 of the lower forefoot portion 12 can be positioned rearward of the toe section 34 of the upper forefoot portion 14. In this way, the lower forefoot member terminates prior to the toe location.

Thus, the lower forefoot portion 12 is shorter than the upper forefoot portion 14 so that the upper forefoot portion can contact the ground at the toe location and the lower forefoot portion can contact the ground at the ball location between the arch location and the toe location. In one aspect, the lower forefoot member has longitudinal length between about 60% to 90% of a longitudinal length of the upper forefoot member; or between about 60% to 80% of a longitudinal length of the upper forefoot member in another aspect. In this way, the lower forefoot member 12 can extend from the ankle section 42 to a ball location of a natural foot, and the upper forefoot member 14 can extend from the ankle section 26 past the ball location to the toe location of a natural foot.

The upper forefoot portion 14 can contact a support surface, such as the ground, floor, inner shoe, lower forefoot, or the like at the toe section 34. Similarly, the lower forefoot portion 12 can contact the ground at the terminal end 48 at or near the ball location. In one aspect, the toe section 34 of the upper forefoot 14 and the terminal end 48 of the lower forefoot 12 can contact the support surface through an inside of a shoe, cosmetic shell, or the like.

Advantageously, the arrangement of having the upper forefoot portion contact the support surface at the toe location and the lower forefoot portion contact the support surface at the ball location provides for a relatively stiffer resiliency through high load portions of a user's gait and also allows the foot to have a softer resiliency when the user assumes a terminal stance. For example, both the upper forefoot portion 14 and the lower forefoot portion 12 can contact the ground during a walking gait or step motion such that a lesser stiffness is felt by the user when only the upper forefoot portion 14 is contacting the ground, for example during a toe-off motion or toe standing position. Additionally, a greater stiffness is felt by the user when both the upper forefoot portion 14 and the lower forefoot portion 12 are contacting the ground together.

Thus, when the lower forefoot portion 12 is contacting the ground, energy can be transferred from the lower forefoot portion 12 to the upper forefoot portion 14 and the two portions can combine to provide a stiffer resiliency or resistance to loads applied to the prosthetic foot 10 during walking motions. In contrast, when the user is simply standing in place, or assumes a terminal stance position, the toe section 34 of the upper forefoot portion 14 can be the only section contacting the ground and, thus, a lesser resistance or softer resiliency can be felt by the user.

In addition, the pair of longer and shorter forefoot members provides multiple axes of rotation of the resilient spring members making up the upper and lower forefoot portions. The combined forefoot members have a first axis of rotation while the upper forefoot member alone has a different second axis of rotation. Advantageously, multiple axes of rotation provide a more natural feel of the prosthetic foot as the user moves through a walking or running motion.

The attachment section 22 and the arch section 30 of the upper forefoot portion 14 can be relatively straight or linear, and can extend forwardly and rearwardly, or in a posterior and anterior direction. Similarly, the attachment section 38 and the partial arch section 46 of the lower forefoot portion can be relatively straight or linear, and can extend forwardly and rearwardly, or in a posterior and anterior direction. Curved or angled sections can be formed between the straight sections. The straight and curved sections can provide multiple spring elements.

The entire foot 10, or the upper forefoot portion 14 and lower forefoot portion 12 can be energy-storing members that flex and bend under a load to store energy. The energy storing members can also be resilient such that the members can return to an original configuration when the load on the foot is released to release the stored energy. Thus, the arch section 30 can displace towards the ankle section 26 of the upper forefoot portion 14. Similarly, the partial arch section 46 can displace towards the ankle section 42 of the lower forefoot portion 12. In this way, the lower forefoot portion 12 and upper forefoot portion 14 can provide vertical shock absorption in that the lower forefoot portion 12 and upper forefoot portion 14 can compress to absorb shock and/or loading in order to provide a cushion during use.

The upper forefoot portion 14 and the lower forefoot portion 12 can include or be formed of a flexible and resilient material. For example, the material can be a composite with fibers disposed in a resin matrix. The fiber can be disposed in unidirectional, mat or weave with several layers. As the amputee steps, or pivots forward, on the prosthetic foot 10, the upper forefoot portion 14 and the lower forefoot portion 12 can deflect. Because the upper forefoot portion 14 and lower forefoot portion 12 are made of a resilient material, the upper forefoot portion 14 and the lower forefoot portion 12 can act as a spring, and store the energy to be released as the user moves forward. Similarly, because the upper and lower forefoot portions 14 and 12 respectively are made of a resilient material the upper and lower forefoot portions can return to an original shape.

The foot 10 can also include an attachment member (not shown) to attach the upper forefoot portion 14 to a socket configured for the specific needs of the amputee. The attachment member can be coupled to either or both of the attachment sections 22 and 38 of the upper forefoot portion 14 and the lower forefoot portion 12. Such sockets typically have a portion adapted for standard attachment. It is of course understood that any type of suitable fastener or connection can be used to couple the attachment member to the attachment sections 22 and 38, including for example, screws, clips, etc.

The attachment sections 22 and 38 can be oblique, or can be disposed at an oblique angle with respect to a support surface or the stump of an amputee. In addition, the attachment member can include a lower oblique surface. The attachment sections 22 and 38 of the forefoot and ankle portions 14 and 12 can include an upper oblique surface 72 that can match and attach to the lower oblique surface. Alternatively, the attachment sections 22 and 38 can be vertically oriented or horizontally oriented with respect to a support surface.

The upper and lower oblique surfaces, can be oblique or oriented at an oblique angle. In one aspect, the attachment sections 22 and 38 can be oriented between approximately 20 and 70 degrees with respect to a horizontal axis. In another aspect, the attachment sections 22 and 38 can be oriented between approximately 30 and 60 degrees with respect to a horizontal axis. In another aspect, the attachment sections 22 and 38 can be oriented at approximately 45 degrees with respect to a horizontal axis, as shown in FIG. 1.

As illustrated in FIG. 2, a prosthetic foot device, indicated generally at 100, in accordance with another embodiment of the present invention is shown for absorbing shock and cushioning a limb or stump of an amputee. The prosthetic foot device 100 can be similar in many respects to the foot device 10 described above and shown in FIG. 1. The prosthetic foot device 100 can have an elongated lower forefoot portion 112 and an elongated, upper forefoot portion 14. Additionally, the prosthetic foot device can have an energy transfer member 150 disposed between the arch section 30 of the upper forefoot portion and the terminal end 148 of the lower forefoot portion.

The energy transfer member 150 can compress as the lower forefoot portion 112 flexes or displaces during use in order to cushion or absorb loading between the upper forefoot portion and the lower forefoot portion. The energy transfer member 150 can variably transfer energy from the lower forefoot portion 112 to the upper forefoot portion 14, ranging from a small amount of energy during small deflections, to a large amount of energy during large deflections. The energy transfer member 150 can include a foam material, compressible bladders, pistons, variable viscosity fluid, or the like. The energy transfer member 150 can also provide extra strength and extra stiffness for strenuous activities.

As illustrated in FIGS. 3-6, a prosthetic foot device, indicated generally at 200, in accordance with another embodiment of the present invention is shown for absorbing shock and cushioning a limb or stump of an amputee. The prosthetic foot device 200 can be similar in many respects to the foot device 10 described above and shown in FIG. 1, or the prosthetic foot device 100 described above and shown in FIG. 2. The prosthetic foot device 200 can have an elongated lower forefoot portion 12 and an elongated, upper forefoot portion 14. Additionally, the prosthetic foot device 200 can have a primary elongated ankle portion 212 and a secondary elongated ankle portion 214.

The primary elongated ankle portion 212 extends rearwardly and downwardly through an attachment section 222, downwardly through an ankle section 226, forwardly and downwardly through an intermediate section 246 under the ankle section 42 of the lower forefoot portion 12, and rearwardly and downwardly through a heel section 250. The heel section 250 is positioned at a heel location of a natural heel. Thus, the ankle portion 212 can have a generally or substantially s-shaped profile. The attachment section 222 and the ankle section 226 of the ankle portion 212 can match and abut to the attachment section 38 and ankle section 42 of the lower forefoot portion 12.

The secondary elongated ankle portion 214 can reinforce the primary ankle portion 212 and provide extra strength and/or extra stiffness for strenuous activities. The secondary ankle portion 214 or reinforcement member can be disposed adjacent or proximate to the primary ankle portion 212. The secondary ankle portion 214 can extend rearwardly through an upper attachment section 238 attached to the attachment section 22 of the upper forefoot portion 14, downwardly through an ankle section 242, forwardly under the ankle section 226 of the primary ankle portion 212, and rearwardly to a heel section 260 positioned above the heel section 250 of the primary ankle portion 212. Thus, during extreme use or deflection of the primary ankle portion 212, the secondary ankle portion 214 or reinforcement member can be engaged. Additionally, the stiffness or strength of the primary ankle portion and the secondary ankle portion can be configured so that the heel section 250 of the primary ankle portion 212 contacts or engages the heel section 260 of the secondary ankle portion 214 based on the user's body weight, such as at 1 gravity.

Figure 7:
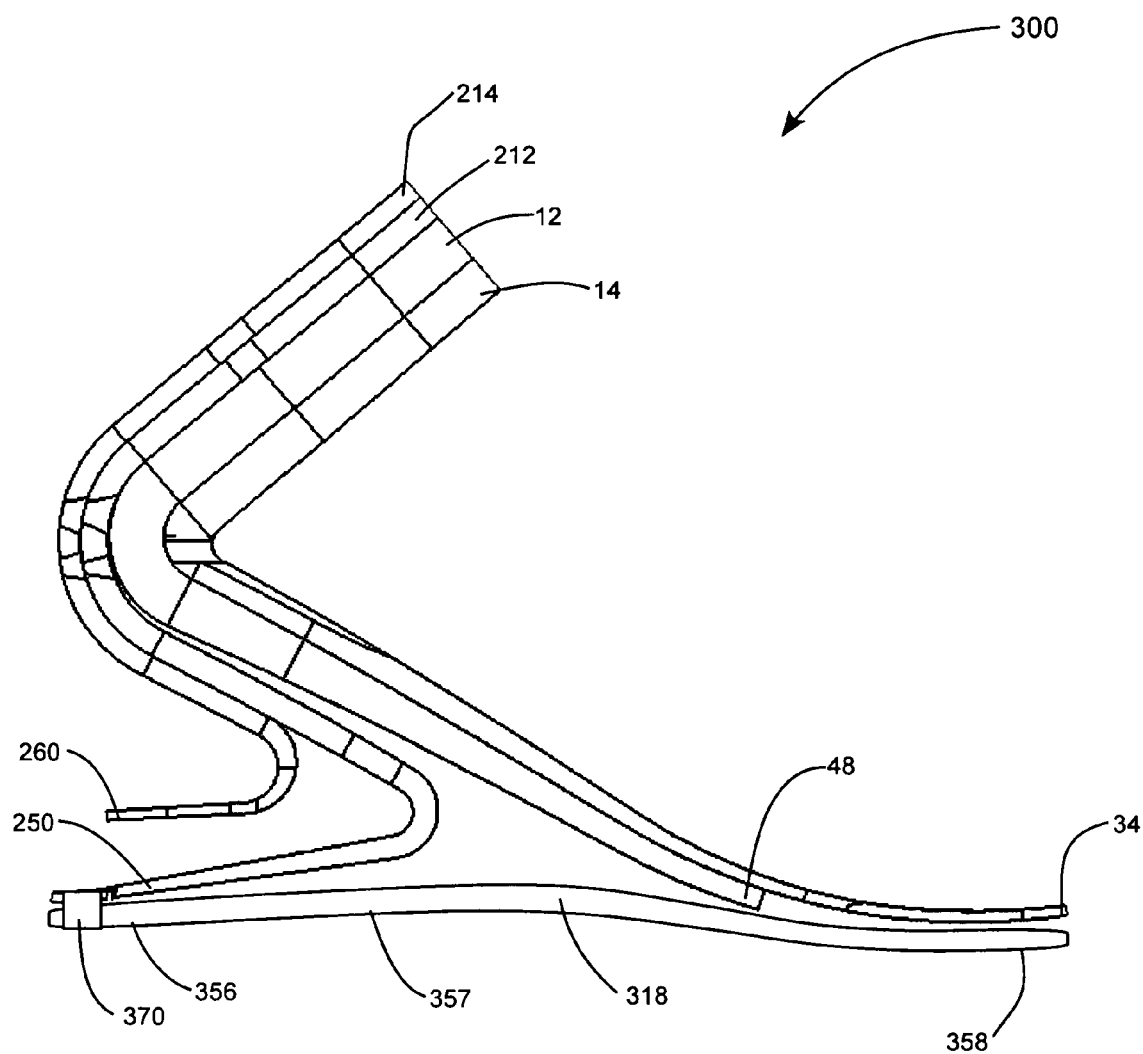
FIG. 7 is a side view of a prosthetic foot device in accordance with another embodiment of the present invention.

As illustrated in FIG. 7, a prosthetic foot device, indicated generally at 300, in accordance with another embodiment of the present invention is shown for absorbing shock and cushioning a limb or stump of an amputee. The prosthetic foot device 300 can be similar in many respects to the foot device 200 described above and shown in FIGS. 3-6. The prosthetic foot device 300 can have an elongated lower forefoot portion 12, an elongated, upper forefoot portion 14, a primary elongated ankle portion 212, and a secondary elongated ankle portion 214. Additionally, the prosthetic foot device 300 can include a lower footplate 318.

The lower footplate 318 can be disposed under the lower forefoot portion 12 and the upper forefoot portion 14, and can extend a length of the foot from the heel to the toe. The lower footplate 318 can be attached to the rear ankle portion 212. The lower footplate 318 can include a heel section 356 attached to the heel section 250 of the primary ankle portion 212. The attachment of the lower footplate 318 to the primary ankle portion 212 can form the primary or only attachment of the footplate 318 to the prosthetic foot 300. The attachment 370 can be formed by wrapping the heel sections 250 and 356 with fibers in a resin matrix. The lower footplate 318 can extend forwardly through the heel section 356, through an arch section 357, and to a toe section 358. The heel section 356 is disposed at a heel location of a natural foot. Likewise, toe section 358 is positioned at a toe location of a natural foot. A gap can be formed between the toe section 358 of the lower footplate 318 and the toe section 34 of the upper forefoot 14 so that the toe sections 34 and 358 are not positively or directly attached. A cushion member (not shown) can be disposed between the toe sections 34 and 358. The cushion member can be formed of a flexible material that can compress as the toe section 358 of the lower footplate 318 moves towards the toe section 34 of the upper forefoot 14.

Figure 8:
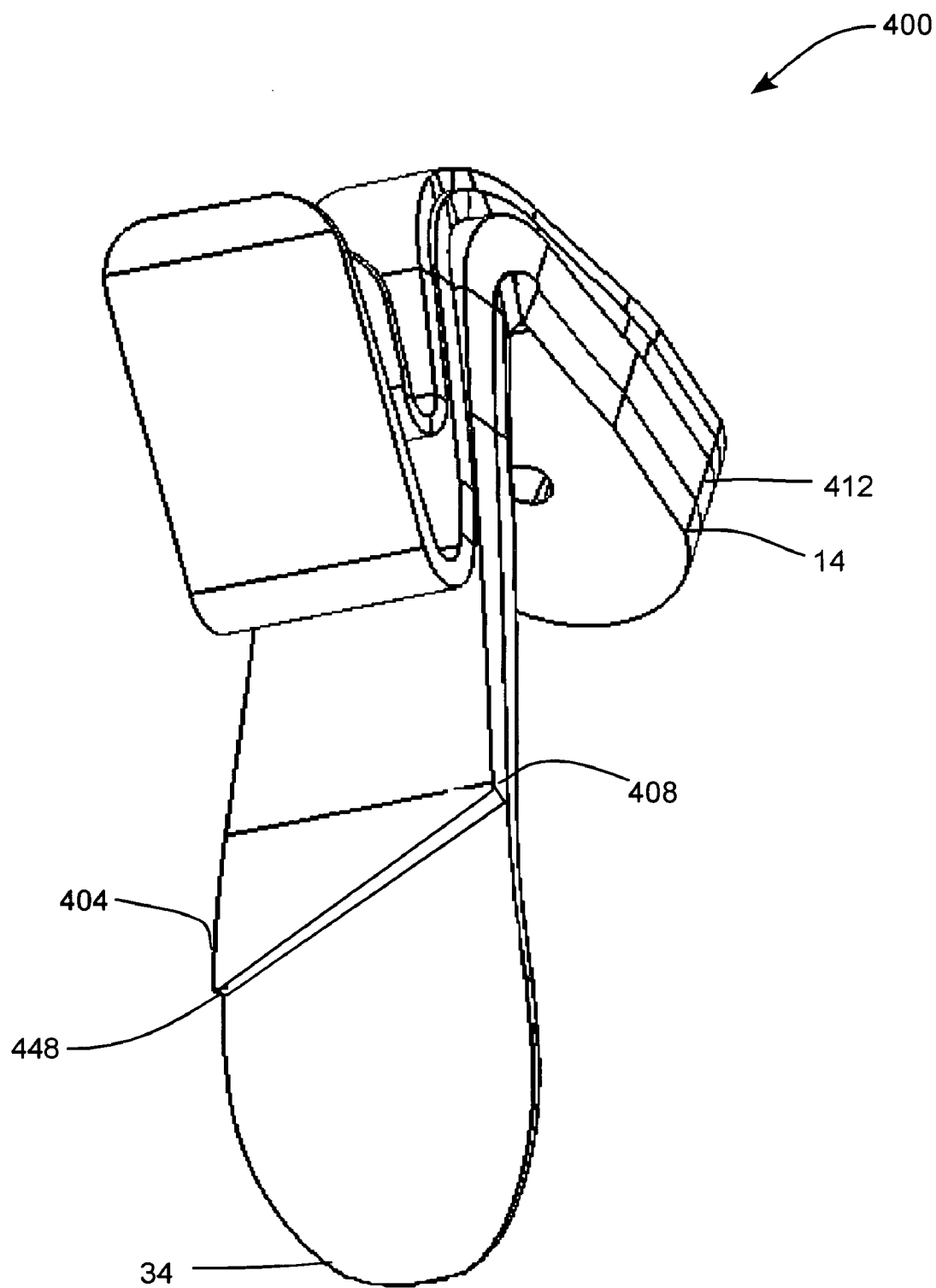
FIG. 8 is a bottom perspective view a prosthetic foot device in accordance with another embodiment of the present invention.

Referring to FIG. 8, another prosthetic foot device, indicated generally at 400, in accordance with another embodiment of the present invention is shown for absorbing shock and cushioning a limb or stump of an amputee. The prosthetic foot device 400 can be similar in many respects to the foot devices described above. The prosthetic foot device 400 can have an elongated lower forefoot portion 412, an elongated, upper forefoot portion 14. The terminal end 448 of the lower forefoot portion 412 can be positioned rearward of the toe section 34 of the upper forefoot portion 14. In this way, the lower forefoot member terminates prior to the toe location. In addition, the terminal end 448 can terminate at an angle with respect to a longitudinal axis of the foot such that one side of the lower forefoot portion 412, such as the medial side 404, is longer than the other side, such as the lateral side 408. The terminal end 448 can form a non-orthogonal or non-perpendicular angle with respect to the longitudinal axis. Thus, the lower forefoot portion 412 and the angled terminal end 448 can provide greater stiffness on one side, such as the side corresponding to the big toe. It will be appreciated that the angled terminal end 448 of the foot device 400 shown in FIG. 8 can be applied to the other embodiments described herein.

Figure 9:
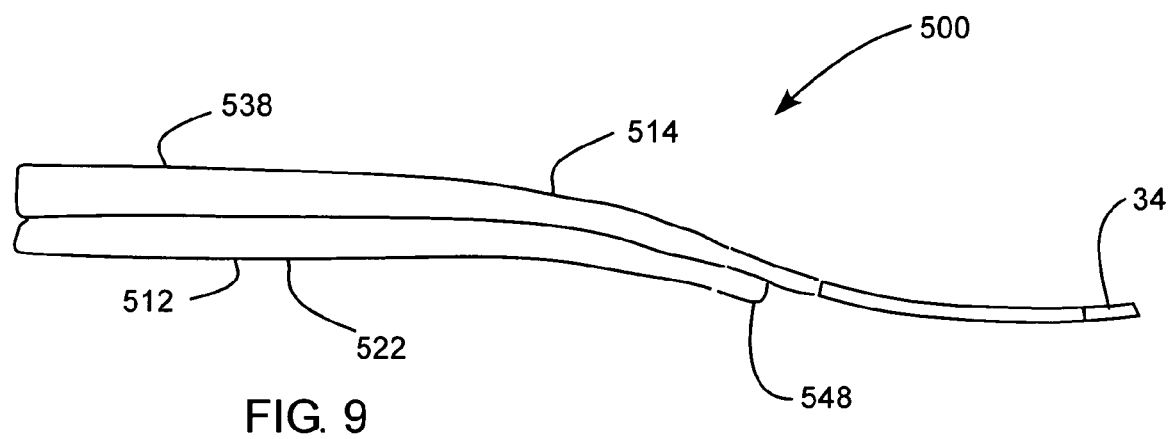
FIG. 9 is a side view of a prosthetic foot device in accordance with another embodiment of the present invention.

Referring to FIG. 9, another prosthetic foot device, indicated generally at 500, in accordance with another embodiment of the present invention is shown for absorbing shock and cushioning a limb or stump of an amputee. The prosthetic foot device 500 can be similar in many respects to the foot devices described above. The prosthetic foot device 500 can have an elongated lower forefoot portion 512, an elongated, upper forefoot portion 514. The terminal end 548 of the lower forefoot portion 512 can be positioned rearward of the toe section 34 of the upper forefoot portion 514. In this way, the lower forefoot member terminates prior to the toe location. In addition, the foot 500, or the upper and lower forefoot portions 514 and 512 can be configured for a lower profile that is more horizontal and which extend forwardly from an attachment section 522 and 538, and down and forward through an arch section.

With respect to each of the embodiments of the prosthetic feet described herein, the terminal end of the shorter lower footplate can have an angled cut to be more tapered at the end and fit better between the upper footplate and the ground. Additionally, a cosmetic shell, or comesis, can be disposed around the feet described above.

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth herein.

What is claimed is:

1. A prosthetic foot device, comprising:
   a pair of elongated forefoot members including an upper forefoot member disposed over a lower forefoot member, each forefoot member extending from an attachment section configured to be coupled to a limb of an amputee;
   the lower forefoot member extending to a termination point at a ball location of a natural foot and under the upper forefoot member;
   the upper forefoot member extending past the termination point of the lower forefoot member to a termination point at a toe location of a natural foot;
   the upper forefoot member and the lower forefoot member forming elongated springs that bend under load to store energy and return to an original configuration when load is released to release energy; and
   an entire length of the lower forefoot member being parallel to the upper forefoot member with respect to a side view and disposed adjacent the upper forefoot member by less than a thickness of one of the forefoot members, wherein the upper forefoot member is substantially arcuate with curved sections, straight sections or both, and extending 1) rearwardly and downwardly through the attachment section, 2) downwardly through an ankle section positioned at an approximate ankle location of a natural foot, 3) forwardly through an arch section, and 4) forwardly to the termination point at the toe location of a natural foot; and the lower forefoot member is substantially arcuate with curved sections, straight sections or both, and extending 1) rearwardly and downwardly through the attachment section, 2) downwardly through an ankle section, and 3) forwardly through an arch section under the arch section of the upper forefoot portion to the termination point at the ball location of a natural foot.

2. A device in accordance with claim 1, wherein the lower forefoot member has a longitudinal length between about 60% to 90% of a longitudinal length of the upper forefoot member.

3. A device in accordance with claim 1, wherein the upper forefoot member contacts a support surface at the termination point of the upper forefoot member and the lower forefoot member contacts the support surface at the termination point of the lower forefoot member.

4. A device in accordance with claim 1, further comprising a cushion member disposed between the upper forefoot member and the lower forefoot member.

5. A device in accordance with claim 1, further comprising:
   a primary elongated ankle member extending from an upper attachment section attached to the attachment section of the lower forefoot member, downwardly through an ankle section, forwardly under an ankle section of the lower forefoot member, and rearwardly to a heel section positioned at a heel location of a natural heel.

6. A device in accordance with claim 5, further comprising:
   a secondary elongated ankle member extending from an upper attachment section attached to the upper attachment section of the primary elongated ankle member, downwardly through an ankle section, forwardly under the ankle section of the primary elongated ankle member, and rearwardly to a heel section positioned above the heel section of the primary elongated ankle portion.

7. A device in accordance with claim 5, further comprising:
   a lower footplate disposed under the forefoot members and the primary elongated ankle member and extending substantially from the toe location to the heel location.

8. A device in accordance with claim 5, wherein the upper attachment sections of the upper and lower forefoot members and the upper attachment section of the primary elongated ankle member are disposed at an oblique angle with respect to a support surface.

9. A device in accordance with claim 1, wherein a terminal end of the lower forefoot member forms a non-orthogonal angle with respect to the longitudinal axis of the device in a side to side direction with one lateral side of the lower forefoot member being longer than another lateral side of the lower forefoot member.

10. A device in accordance with claim 1, wherein the pair of elongated forefoot members further extend from the attachment section downward through an ankle section positioned at an ankle location of a natural foot.

11. A prosthetic foot device, comprising:
   a) an elongated upper forefoot portion that is substantially arcuate with curved sections, straight sections or both, and extending 1) rearwardly and downwardly through an upper attachment end configured to be coupled to a limb of an amputee, 2) downwardly through an ankle section positioned at an approximate ankle location of a natural foot, 3) forwardly through an arch section, and 4) forwardly to a toe section positioned at a toe location of a natural foot;
   b) an elongated lower forefoot portion that is substantially arcuate with curved sections, straight sections or both, and extending 1) rearwardly and downwardly through an upper attachment end attached to the upper attachment end of the upper forefoot portion, 2) downwardly through an ankle section, and 3) forwardly through an arch section under the arch section of the upper forefoot portion to a terminal end positioned at a ball location of a natural foot and rearward of the toe section of the upper forefoot;
   c) the upper forefoot member and the lower forefoot member forming vertically oriented arcs extending in a posterior and anterior direction;
   d) the upper forefoot portion and the lower forefoot portion forming elongated springs that bend under load to store energy and return to an original configuration when load is released to release energy, with the arch section of the upper forefoot portion displacing towards the ankle section of the upper forefoot portion, and the arch section of the lower forefoot portion displacing towards the ankle section of the lower forefoot portion, under load; and
   e) the upper and lower forefoot portions being disposed directly adjacent one another with no gap between the upper forefoot member and the lower forefoot member.

12. A device in accordance with claim 11, wherein the lower forefoot portion has longitudinal length between about 60% to 90% a longitudinal length of the upper forefoot portion.

13. A device in accordance with claim 11, wherein the upper forefoot portion contacts a support surface at a termination point of the upper forefoot portion and the lower forefoot portion contacts the support surface at a termination point of the lower forefoot portion.

14. A device in accordance with claim 11, further comprising:
   a primary elongated ankle portion extending 1) rearwardly through an upper attachment section attached to the attachment end of the lower forefoot portion, 2) downwardly through an ankle section 3) forwardly under an ankle section of the lower forefoot portion, and 4) rearwardly to a heel section positioned at a heel location of a natural heel.

15. A device in accordance with claim 14, further comprising:
   a secondary elongated ankle portion extending 1) rearwardly through an upper attachment section attached to the upper attachment section of the primary elongated ankle portion, 2) downwardly through an ankle section 3) forwardly under the ankle section of the primary elongated ankle portion, and 4) rearwardly to a heel section positioned above the heel section of the primary elongated ankle portion.

16. A device in accordance with claim 11, further comprising:
   a lower footplate, attached to the upper forefoot portion, and extending rearwardly through 1) a toe section attached to the toe section of the upper forefoot portion, 2) an arch section, and 3) to a heel section positioned at a heel location of a natural foot.

17. A device in accordance with claim 11, wherein the upper attachment end of the upper forefoot portion is disposed at an oblique angle with respect to a support surface.

18. A device in accordance with claim 11, wherein the terminal end of the lower forefoot portion forms a non-orthogonal angle with respect to the longitudinal axis of the device in a side to side direction so that one side of the lower forefoot portion is longer than an opposite side of the lower forefoot portion with one lateral side of the lower forefoot portion being longer than another lateral side of the lower forefoot portion.

19. A prosthetic foot device, comprising:
   a pair of elongated forefoot members including an upper forefoot member disposed over and directly adjacent a lower forefoot member with no gap between the upper forefoot member and the lower forefoot member, and the forefoot members extending from attachment ends attached together at a common location and configured to be coupled to a limb of an amputee;
   an entire length of the lower forefoot member being parallel to the upper forefoot member with respect to a side view;
   the upper forefoot member and the lower forefoot member forming elongated springs that bend under load to store energy and return to an original configuration when load is released to release energy;
   the lower forefoot member extending to a termination point at a ball location of a natural foot and under the upper forefoot member; and
   the upper forefoot member extending past the termination point of the lower forefoot member to a termination point at a toe location of a natural foot, wherein the upper forefoot member is substantially arcuate with curved sections, straight sections or both, and extending 1) rearwardly and downwardly through the attachment section, 2) downwardly through an ankle section positioned at an approximate ankle location of a natural foot, 3) forwardly through an arch section, and 4) forwardly to the termination point at the toe location of a natural foot; and
   the lower forefoot member is substantially arcuate with curved sections, straight sections or both, and extending 1) rearwardly and downwardly through the attachment section, 2) downwardly through an ankle section, and 3) forwardly through an arch section under the arch section of the upper forefoot portion to the termination point at the ball location of a natural foot.

* * * * *